(12) United States Patent
Luyt et al.

(10) Patent No.: US 8,623,326 B2
(45) Date of Patent: Jan. 7, 2014

(54) GHRELIN ANALOGUES

(75) Inventors: Leonard G. Luyt, London (CA); Dina Rosita, London (CA)

(73) Assignee: University of Western Ontario, London, Ontario (CA)

( * ) Notice: Subject to any disclaimer, the term of this patent is extended or adjusted under 35 U.S.C. 154(b) by 71 days.

(21) Appl. No.: 12/994,259

(22) PCT Filed: May 22, 2009

(86) PCT No.: PCT/CA2009/000693
§ 371 (c)(1),
(2), (4) Date: Jan. 14, 2011

(87) PCT Pub. No.: WO2009/140763
PCT Pub. Date: Nov. 26, 2009

(65) Prior Publication Data
US 2011/0110855 A1        May 12, 2011

Related U.S. Application Data

(60) Provisional application No. 61/071,894, filed on May 23, 2008.

(51) Int. Cl.
*A61K 51/08* (2006.01)
*A61K 38/03* (2006.01)
*G01N 33/567* (2006.01)

(52) U.S. Cl.
USPC .......................... 424/1.69; 514/9.7; 530/324

(58) Field of Classification Search
None
See application file for complete search history.

(56) References Cited

U.S. PATENT DOCUMENTS 7,173,109 B2    2/2007  Enderle et al.
2010/0254994 A1 * 10/2010 Raso .................... 424/158.1

FOREIGN PATENT DOCUMENTS

EP            1524274       3/2008
WO    WO 2009/140763      11/2009

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Definition of analogue, from http://cancerweb.ncl.ac.uk/cgi-bin/omd?analogue, pp. 1-5, accessed Jul. 7, 2005.*
Definition of aliphatic, from http://www.merriam-webster.com/dictionary/aliphatic, pp. 1-3, accessed Mar. 8, 2013.*
Definition of aromatic, from http://www.merriam-webster.com/dictionary/aromatic, pp. 1-3, accessed Mar. 8, 2013.*
Definition of derivative, from http://cancerweb.ncl.ac.uk/cgi-bin/omd?query=derivative, pp. 1-5, accessed Jul. 7, 2005.*
Radioisotopes in Medicine, from http://www.world-nuclear.org/info/Non-Power-Nuclear-Applications/Rodioisotopes/Radioisotopes-in-Medicine, pp. 1-7, accessed Mar. 8, 2013.*
Matsumoto et al, Structure—Activity Relationship of Ghrelin: Pharmacological Study of Ghrelin Peptides, Biochemical and Biophysical Research Communications, 2001, 287, pp. 142-146.*
Yang et al., Identification of the Acyltransferase that Octanoylates Ghrelin, an Appetite-Stimulating Peptide Hormone. Cell, vol. 132, Issue 3, 387-396, Feb. 8, 2008.
Van Craenenbroeck et al. Ala-scan of ghrelin (1-14): interaction with the recombinant human ghrelin receptor. Peptides. Jun. 2004;25(6):959-65.
Leite-Moreira et al. Physiological, pathological and potential therapeutic roles of ghrelin. Drug Discovery Today, vol. 12, Nos. 7/8, Apr. 2007.
Kageyama, et al. Visualization of ghrelin-producing neurons in the hypothalamic arcuate nucleus using ghrelin-EGFP transgenic mice. Regulatory Peptides. Jan. 10, 2008;145(1-3):116-21. Epub Sep. 25, 2007.

* cited by examiner

*Primary Examiner* — Julie Ha
*Assistant Examiner* — Li Ni Komatsu (57) ABSTRACT

Ghrelin analogues having high affinity for a target receptor in diseased cells are provided, as well as methods of diagnosis and treatment utilizing such analogues.

7 Claims, 6 Drawing Sheets

(SEQ ID NO: 1)

(SEQ ID NO: 6)

(SEQ ID NO: 4)

(SEQ ID NO: 7)

B)

(SEQ ID NO: 8)

GHRELIN ANALOGUES

CROSS-REFERENCE TO RELATED APPLICATION

This application is a national entry filing of PCT/CA2009/000693 which claims priority to U.S. Provisional Patent Application No. 61/071,894 filed on May 23, 2008, the contents of each of which are hereby incorporated by reference in their entirety.

FIELD OF THE INVENTION

The present invention relates to ghrelin analogues and, in particular, to ghrelin analogues having a specific affinity for ghrelin receptors such as, human growth hormone secretagogue receptors.

BACKGROUND OF THE INVENTION

Human Growth Hormone Secretagogue Receptor (GHSR), a member of the G Protein-Coupled Receptors (GPCR) family, was identified in 1996 as a 7 transmembrane domain 366 amino-acid protein that is responsible for the regulation of the growth hormone (GH) secretion. This receptor is mainly expressed in the hypothalamus, pituitary cells, and a number of peripheral tissues. Expression of the GHSR has been reported in various types of tumors, including breast carcinomas, prostate cancer cell lines, ovarian tumors, testicular tumors, pancreatic endocrine tumors, and intestinal carcinoids. The presence of high affinity and specific binding sites on GHSR in the neoplastic cells which are absent in the corresponding normal tissues has been demonstrated in at least 3 different human breast carcinoma cell lines and pancreatic endocrine tumors.

Figure 1:
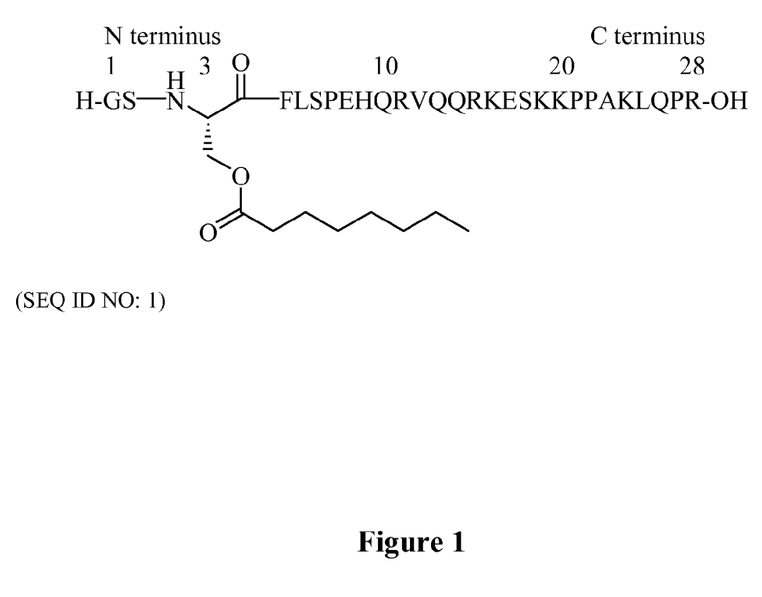
FIG. 1 illustrates the chemical structure of ghrelin.

Ghrelin, as shown in FIG. 1, was discovered in 1999 by Kojima et. al. and is the natural ligand for the GHSR. Ghrelin is a 28-amino acid peptide hormone in which serine-3 residue is n-octanoylated. This hormone plays an important role in the stimulation of GH secretion through binding with GHSR along with some other functions including appetite regulation. Ghrelin binds to the GHSR with high affinity and specificity, resulting in a ghrelin-GHSR complex that is internalized.

SUMMARY OF THE INVENTION

Analogues of ghrelin have now been developed which exhibit specific receptor-binding activity for diagnostic and therapeutic use.

Thus, in one aspect of the invention, a receptor-binding ghrelin analogue is provided, wherein said analogue is modified to incorporate a functional entity.

In another aspect of the invention, a method of detecting a disease in a mammal is provided comprising the steps of:
1) administering to the mammal a receptor-binding ghrelin analogue modified to incorporate an imaging agent; and
2) determining the amount of ghrelin receptor at a target site in the mammal by detecting the amount of bound imaging agent, wherein an amount of ghrelin receptor that differs from normal an amount is indicative of disease.

In another aspect of the invention, a method of treating a disease associated with ghrelin receptor in a mammal is provided comprising administering to the mammal a ghrelin analogue that binds to the ghrelin receptor, wherein said analogue is modified to incorporate a therapeutic agent effective to treat the disease.

In a further aspect of the invention, a kit is provided comprising a receptor-binding ghrelin analogue and a functional entity for attachment to the ghrelin analogue.

In a further aspect of the invention, an article of manufacture is provided comprising packaging material and a receptor-binding ghrelin analogue, wherein the packaging material is labelled to indicate that the ghrelin analogue is adapted for linkage to a functional entity.

These and other aspects of the present invention will become apparent by reference to the following detailed description and drawings.

DETAILED DESCRIPTION

Receptor-binding ghrelin analogues are provided which are modified to incorporate a functional entity.

The term "ghrelin" is used herein to refer to mammalian ghrelin, a peptide hormone, including human ghrelin as depicted in FIG. 1, having the amino acid sequence, GSS(n-octanoyl)FLSPEHQRVQQRKESKKPPAKLQPR (SEQ ID No. 1), as well as other forms of ghrelin, for example, from other mammalian species.

The term "receptor-binding" refers to the ability of a ghrelin analogue to bind to a target receptor including, but not limited to, GHSR, and particularly to receptors or receptor sites which are prevalent in a disease state such as specific GHSR binding sites in cancer cells.

The term "analogue" refers to ghrelin which is altered from its native form. A ghrelin analogue may, thus, incorporate alterations in structure including side chain modifications, terminal modifications, truncation and amino acid substitutions, for example by conservative amino acid replacement such as substitution of glutamic acid with aspartic acid, or substitution of lysine with arginine, by non-conservative amino acid replacements, or by amino acid replacements with un-naturally occurring amino acids (e.g. D-lysine, D-aspartic acid, D-glutamic acid, diaminopropanoic acid, diaminobutyric acid, ornithine, allylglycine, aminoadipic acid, homocysteine, or related molecules) that do not adversely affect the receptor-binding activity of the analogue. Preferably, alterations to the analogue function to increase in vivo stability and penetration to permit the analogue to reach target binding sites. Furthermore, alterations will preferably improve or retain strong affinity for ghrelin receptor binding sites. For example, substituting the glutamic acid at position-8 of native ghrelin with arginine or lysine increases the potency of GHSR stimulation.

The analogues of the invention comprise a peptide-derived entity based on the chemical structure of the 28-amino acid peptide ghrelin. The amino acid sequence of the analogue is selected to facilitate affinity for ghrelin binding sites. Truncation of the C-terminal section of ghrelin is preferred in order to minimize the size of the entity. In order to maintain receptor-binding activity, ghrelin analogues according to the invention comprise at least amino acids at positions 1-5 of the native ghrelin peptide hormone (as depicted in FIG. 1), and may additionally comprise one or more amino acids from positions 6 to 28. Preferably, ghrelin analogues according to the invention comprise at least amino acids at positions 1-7 of ghrelin, and more preferably at least amino acids at positions 1-10 of ghrelin.

The present ghrelin analogues may additionally be modified at the amino acid side chain groups. Such modifications may include modifications which increase stability, or otherwise confer on the analogue a desirable property. In one embodiment, the ghrelin analogues include a modification at the amino acid at position 3 which is an n-octanoyl-substituted serine residue in native ghrelin. As one of skill in the art will appreciate, modifications at position 3 include those that do not adversely affect the receptor binding activity of the analogue, and thus, include modifications which retain the properties of the native n-octanoyl substituent, including suitable lipophilicity and neutrality, at least to the extent required to retain sufficient receptor binding. In this regard, suitable modifications may include replacement of the n-octanoyl substituent with aliphatic chains e.g. comprising from about 4 to about 16 carbon atoms; aromatic entities e.g. phenyl, biphenyl, napthyl, or substituted derivatives thereof. In addition, the ester bond linking the n-octanoyl group to the peptide (which may readily undergo hydrolysis) may be replaced with a more stable linkage such as an amide linkage.

The present ghrelin analogues incorporate a functional entity. The term "functional entity" is used herein to refer to any entity suitable for attachment to the ghrelin analogues that imparts on the analogue a particular function, including but not limited to, an imaging agent or other detectable label, a therapeutic agent, or any other entity that may require delivery to a ghrelin receptor.

For example, the ghrelin analogue may incorporate an imaging agent to render the analogue useful in any one of various imaging modalities, including but not limited to, single photon emission computed tomography (SPECT), positron emission tomography (PET), magnetic resonance imaging (MRI), computed tomography (CT), optical, and ultrasound (US). For SPECT, a gamma emitting radionuclide, including but not limited to $^{67}$Ga, $^{99m}$Tc, $^{111}$In, $^{123}$I or $^{123}$I may be used. For PET, a positron emitting radionuclide, including but not limited to $^{18}$F, $^{44}$Sc, $^{64}$Cu, $^{68}$Ga, or $^{94m}$Tc may be used. For MRI, a Gd or other lanthanide may be used. For CT, an iron oxide, or other contrast enhancing unit may be used. For optical imaging, a fluorescent dye such as fluorescein, bromeosin, rhodamine, coumarin, cyanine, or derivatives thereof, including near-infrared dyes. For US, the ghrelin analogue may facilitate delivery of micro-bubbles. In addition, the targeting ability of the ghrelin analogue may be incorporated into a nanoparticle, either polymer-based or as a biological macromolecule, for example viral, to facilitate tumour targeting.

As one of skill in the art will appreciate, well-established methods may be utilized to incorporate the functional entity into the selected ghrelin analogue. The method(s) utilized may vary with the functional entity to be incorporated. The functional entity may be connected to the ghrelin analogue by a direct or indirect bond, via a linker such as an aliphatic chain, or in the case of a metal, through a chelation or organometallic complex.

The functional entity may be situated at any convenient location on the ghrelin analogue, including but not limited to the C-terminus or on a side-chain of an amino acid within the analogue. In a preferred embodiment, the functional entity is attached to the analogue at the amino acid residue at position 3 of the analogue, the position of the octanoylated serine in the native ghrelin peptide. In this regard, the n-octanoyl group may be modified or replaced as previously described to serve as a suitable site of attachment for the functional entity. To retain receptor affinity, this side-chain may contain from about 2 to about 16 methylene units between the functional group of the side-chain, e.g. the alcohol, thiol or amine functional group of the side-chain, and the location of the functional entity to be attached. This side-chain may also contain other atoms besides carbon, for example ethylene glycol units. Similarly, the functional entity may be situated at other locations within the peptide, for example, linked to another side-chain functional group. In this regard, the functional entity may be linked to a naturally occurring amino acid native to the ghrelin protein (e.g. lysine, aspartic acid, glutamic acid, cysteine) or linked to an unnaturally occurring amino acid (e.g. D-lysine, D-aspartic acid, D-glutamic acid, diaminopropanoic acid, diaminobutyric acid, ornithine, allylglycine, aminoadipic acid, homocysteine, or related molecules) that replaces an amino acid native to ghrelin.

Ghrelin analogues according to the invention are useful in a method of detecting a disease state in a mammal. The term "mammal" is used herein to refer to both human and non-human mammals. The method comprises the step of administering a detectable labelled receptor-binding ghrelin analogue to the mammal. The analogue is capable of specifically binding to a receptor, such as GHSR, that is useful in the diagnosis of disease, for example, cancer, cardiovascular disease, diabetes, disorders of the nervous system (central and peripheral), gastro-intestinal disease, hematological disease, inflammation, and respiratory disease. Administered ghrelin analogue is detected and measured by measuring the amount of retained detectably label, e.g. imaging agent, within the mammal. The detection of an abnormal amount of retained or bound analogue, either abnormally high amounts or abnormally low amounts in comparison to normal amounts that are retained in healthy mammals (i.e. control amounts), is indicative of correspondingly abnormal amounts of ghrelin receptor, which is indicative of disease.

As one of skill in the art will appreciate, a method of detecting disease may also be conducted in vitro. In this case, a suitable biological sample is obtained from a mammal to be diagnosed. Suitable biological samples may include, for example, non-invasively obtained samples such as blood, urine and saliva, as well as invasively obtained samples such as tissue samples obtained by biopsy. The biological sample may also include cells, cultured cell lines, transfected cell lines or commercially available cell lines. Once obtained, a detectably labelled receptor-binding ghrelin analogue is combined with the sample (or a purified or otherwise processed version of the sample, if required) under conditions suitable to permit analogue binding to the target receptor. The sample may then be imaged to detect bound analogue which may then be quantified as described, and a diagnosis made based on a finding of abnormal levels of receptor.

For use in a therapeutic method according to another aspect of the invention, the present ghrelin analogues may incorporate a therapeutic agent as the functional entity for targeted delivery to a ghrelin-binding receptor site associated with a disease state. Examples of therapeutic agents that may be attached to a ghrelin analogue for delivery to a receptor binding site include, but are not limited to, alkylating agents, anti-angiogenic agents, antibiotics, antidiabetics, antifungals, antimicrobials, antimitotics, antimycobacterials, antineoplastics, antiparasitics, antivirals, chemokines, cytokines, cytotoxic agents, hormonal therapeutics, nucleoside analogues, or prodrugs thereof. The therapeutic agent may also be a particle emitting radionuclide, including a beta-emitting radionuclide such as $^{90}$Y, or $^{186}$Re; a beta/gamma emitting radionuclide such as $^{47}$Sc, $^{153}$Sm, $^{177}$Lu, or $^{188}$Re; or alpha-emitting radionuclides such as $^{213}$Bi, $^{223}$Ra, or $^{225}$Ac. The therapeutic agent may alternatively be a non-radioactive metal such as rhenium, indium, and the like, which may be used for therapeutic intervention or as a chemical standard for biological evaluations.

The ghrelin analogue modified to incorporate a selected therapeutic agent is administered to a mammal in the treatment of a target disease, e.g. a ghrelin receptor-related condition. In this regard, the ghrelin analogue may be administered to the mammal by any suitable route of administration, including for example, oral, parenteral, by injection, intravenous, by inhalation, topical, and any other suitable administrable routes.

The ghrelin analogue modified to incorporate a therapeutic agent may be administered in the form of a pharmaceutical composition comprising the analogue and at least one pharmaceutically acceptable adjuvant. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods.

In accordance with the invention, a therapeutically effective amount of a ghrelin analogue-containing therapeutic agent is administered to a mammal in the treatment of disease. The term "therapeutically effective amount" is an amount of the therapeutic agent indicated for treatment of a target disease while not exceeding an amount which may cause significant adverse effects. Appropriate dosages, thus, will vary on many factors including the nature of the target disease and selected therapeutic agaent to used in the treatment protocol. Appropriate dosages for use can readily be determined by one of skill in the art.

In another aspect, a kit is provided comprising a ghrelin analogue along with a functional entity to be incorporated into the analogue. The functional entity may be any entity suitable for attachment to the analogue to impart onto the analogue a selected utility, including but not limited, an imaging agent or other detectable label, a therapeutic agent and the like. The kit may also include one or more reagents to facilitate the attachment of the selected functional entity to the ghrelin analogue. The kit may optionally include instructions to facilitate the linkage of the functional entity to the ghrelin analogue. For greater versatility, the kit may comprise a ghrelin analogue along with instructions to link it to one or more desirable functional entities.

Embodiments of the present invention will now be described by reference to the following specific examples which are not to be construed as limiting.

Example 1

Materials and Equipment.

Reagents and solvents were purchased from Sigma-Aldrich, Fluka, NovaBiochem, Peptides International, Strem Chemicals, Toronto Research Chemicals, Chem-Impex, Fisher Scientific, or VWR and were used without further purification unless noted. Dry $CH_2Cl_2$ was prepared by distillation from CaH under argon. Oven-dried or flame-dried apparatus and argon flow were used in all water sensitive reactions. Analytical HPLC was performed using a Grace Vydac Protein/Peptide RP-C18 column 4.6×250 mm, 5 µm and preparative HPLC was performed using a Grace Vydac Protein/Peptide RP-C18 column 22.0×250 mm, 10 µm. The absorbance was detected at wavelengths of 220 nm and 254 nm. A gradient system was used: $H_2O$+0.1% of TFA (solvent A) and $CH_3CN$+0.1% of TFA (solvent B). Flash column chromatography was performed using Merck Silica Gel 60 (230-400 mesh). Analytical TLC was carried out on EMD Silica Gel 60 $F_{254}$ plates. $^1$H and $^{13}$C NMR data was obtained using a Varian Mercury 400, and the chemical shifts were referenced to solvent signals ($CDCl_3$: $^1$H 7.25 ppm, $^{13}$C 77.23 ppm) relative to TMS. Mass spectra were obtained using Finnigan MAT 8200 (HRMS-EI), Micromass LCT (MS-ESI), and Micromass MALDI-LR (MALDI-TOF) mass spectrometers. For compounds containing rhenium, both $^{185}$Re and $^{187}$Re peaks are observed, and the more abundant $^{187}$Re mass are reported in this section. Melting points were determined in open capillary tubes on Mel-temp apparatus without correction.

Peptide Assembly.

Fully-protected resin-bound peptides were synthesized according to the general procedures in Fmoc solid phase peptide synthesis either manually or automated using an APEX 396 peptide synthesizer. Fmoc protected rink amide MBHA resin (loading 0.27 or 0.47 meq/g) was used as the solid support. N-Fmoc amino acids, with strong acid labile protecting groups for side-chain functional groups, were used in general, and N-Boc amino acid was used for the N terminus. Fmoc-diaminopropanoic acid (Dpr), with the β-amine protected with methyltrityl (Mtt), was used for residue-3. Fmoc removal was achieved with treatments of 20% piperidine in N,N-dimethylformamide (DMF) for 10 and 20 minutes and successive washes using DMF and $CH_2Cl_2$ after each treatment. For each amino acid coupling, resin was treated once or twice with 3 eq. of Fmoc or Boc amino acids, 3 eq. of 3-[bis(dimethylamino)methyliumyl]-3H-benzotriazol-1-oxidehexafluorophosphate (HBTU) and 6 eq. of N,N-diisopropylethylamine (DIPEA) in 2 mL of DMF for 30 minutes to 4 hours. Successive washes with DMF, $CH_2Cl_2$, and THF were done following the coupling. Using this general procedure, 12 and 13 were prepared (see FIG. 1).

Peptide Deprotection and Resin Cleavage.

Selective deprotections of amine-Mtt and alcohol-Trt were achieved by shaking the resin with 2% TFA and 5% triisopropylsilane (TIS) in $CH_2Cl_2$ for 2 minutes, followed by successive washes with $CH_2Cl_2$. This treatment was repeated five times. During the solid phase reaction steps, the presence or absence of a free amine group was monitored by the Kaiser test, as described in Anal. Biochem. 1970, 34, 595-598, the relevant contents of which are incorporated herein by reference. When necessary, cleaving a small sample of resin beads (micro-cleave) was performed to obtain a small quantity of representative peptide, for which HPLC and MS analyses were conducted. After all modifications were done, the peptide was deprotected and cleaved from the resin by TFA containing the scavengers water (5% v/v), phenol (5% m/v), TIS (2% v/v) for 2-4 hours. Resin was filtered and rinsed with a small amount of TFA. Peptide was precipitated from the TFA solution using tert-butyl methyl ether (TBME), and collected after centrifugation and decanting. Peptide was then rinsed using TBME and collected again. The resulting solid was redissolved in water with additional $CH_3CN$ when necessary, frozen, and lyophilized to obtain crude peptide as a fine powder. Purification of the peptide was conducted through preparative HPLC runs and the purity of the isolated material was determined by analytical HPLC.

Methyl 6-hydroxy-hexanoate (14a).

This compound was prepared from ε-caprolactone (10.01 g, 87.7 mmol) according to a literature procedure, as described in Duffey et al. J. Chem. Soc. Perkin Trans. 1 2002, 1555-1563, the relevant contents of which are incorporated herein by reference. The colorless oil 14a was obtained with a yield of 77%. $^1$H-NMR (400 MHz, $CDCl_3$, $\delta_H$ ppm): 3.63 (3H, s, $CO_2CH_3$), 3.61 (2H, t, $^3J_{H-H}$=6.5 Hz, HO—$CH_2$), 2.30 (2H, t, $^3J_{H-H}$=7.4 Hz, $CH_2CO_2$), 1.50-1.68 (4H, m, $2CH_2$), 1.31-1.44 (2H, m, $CH_2$).

Methyl-12-hydroxy-dodecanoate (14c).

Concentrated $H_2SO_4$ (0.2 mL) was added to a solution of oxacyclotridecan-2-one (850 mg, 4.3 mmol) in 20 mL of methanol and stirred for 1 day. Methanol was removed under reduced pressure and the aqueous residue was extracted with diethyl ether 3 times. The combined organic layers were washed with saturated $NaHCO_3$, saturated NaCl, and then dried over $MgSO_4$. The diethyl ether was removed under reduced pressure to yield 874 mg (88%) of 14c as a white solid. $^1$H-NMR (400 MHz, $CDCl_3$, $\delta_H$ ppm): 3.65 (3H, s, $CO_2CH_3$), 3.63 (2H, t, $^3J_{H-H}$=6.6 Hz, HO—$CH_2$), 2.29 (2H, t, $^3J_{H-H}$=7.6 Hz, $CH_2CO_2$), 1.50-1.66 (4H, m, $2CH_2$), 1.22-1.38 (14H, m, $7CH_2$). HRMS (EI): m/z calcd 231.1955 ([M+H]$^+$, $C_{13}H_{27}O_3$), found 231.1954 [M+H]$^+$.

Methyl 6-trityloxy-hexanoate (15a).

Trityl chloride (18.8 g, 67.4 mmol) was added to an ice cold (0° C.) stirring solution of 14a (9.9 g, 67.4 mmol) in 80 mL of pyridine. The reaction mixture was warmed to room temperature and stirred under argon for 2 days, during which time a white byproduct formed. The solvent was removed under reduced pressure, and the resulting material was redissolved in ice cold THF. The insoluble byproduct was removed by filtration, and the filtrate was dried under reduced pressure to obtain 22.6 g (86%) of an orange oil 15a. $^1$H-NMR (400 MHz, $CDCl_3$, $\delta_H$ ppm): 7.43 (6H, m, p-Ar), 7.29 (6, m, m-Ar), 7.22 (3H, m, o-Ar), 3.65 (3H, s, $CO_2CH_3$), 3.05 (2H, t, $^3J_{H-H}$=6.6 Hz, HO—$CH_2$), 2.29 (2H, t, $^3J_{H-H}$=7.5 Hz, $CH_2CO_2$), 1.54-1.71 (4H, m, $2CH_2$), 1.33-1.45 (m, 2H, $CH_2$). HRMS (EI): m/z calcd 388.2038 ($C_{26}H_{28}O_3$), found 388.2039 [M]$^+$.

Methyl-9-trityloxy-nonanoate (15b).

The synthesis procedure of 15a was followed, with 1.37 g (4.9 mol) of trityl chloride, 0.46 g (2.5 mmol) of methyl-9-hidroxy-nonanoate, and 10 mL of pyridine used in the reaction. An insoluble byproduct was removed by filtration in $CH_2Cl_2$ and 10% ethyl acetate in hexanes, and upon solvent removal, 1.02 g (96%) of 15b was obtained as a pale yellow oil. $^1$H-NMR (400 MHz, $CDCl_3$, $\delta_H$ ppm): 7.44 (6H, m, p-Ar), 7.28 (6H, m, m-Ar), 7.22 (3H, m, o-Ar), 3.65 (3H, s, $CO_2CH_3$), 3.03 (2H, t, $^3J_{H-H}$=6.6 Hz, HO—$CH_2$), 2.29 (2H, t, $^3J_{H-H}$=7.5 Hz, $CH_2CO_2$), 1.55-1.65 (4H, m, $2CH_2$), 1.18-1.40 (8H, m, $4CH_2$). HRMS (EI): m/z calcd 430.2508 ($C_{29}H_{34}O_3$), found 430.2514 [M]$^+$.

Methyl-12-trityloxy-dodecanoate (15c).

The synthesis procedure of 15a was followed. Trityl chloride (1412 mg, 5.1 mmol), 14c (583 mg, 2.5 mmol), and pyridine (10 mL) were used and the reaction was prolonged to 3 days. The filtration step was omitted, instead the crude material was purified by flash column chromatography (10% EtOAc in hexanes) yielding 477 mg (40%) of a pale yellow oil 15c. $^1$H-NMR (400 MHz, $CDCl_3$, $\delta_H$ ppm): 7.44 (6H, m, p-Ar), 7.28 (6H, m, m-Ar), 7.21 (3H, m, o-Ar), 3.66 (3H, s, $CO_2CH_3$), 3.03 (2H, t, $^3J_{H-H}$=6.6 Hz, H)—$CH_2$), 2.29 (2H, t, $^3J_{H-H}$=7.5 Hz, $CH_2CO_2$), 1.55-1.65 (4H, m, $2CH_2$), 1.10-1.39 (14H, m, $7CH_2$). HRMS (EI): m/z calcd 472.2977 ($C_{32}H_{40}O_3$), found 472.2968 [M]$^+$.

6-Trityloxyhexanoic acid (16a).

An aqueous solution of 5 M NaOH (17.5 mL, 87.5 mmol) was added to a stirring solution of 15a (20.1 g, 51.6 mmol) in 130 mL of THF and 52.5 mL of water at room temperature. After stirring for 2 days, 3.1 mL of 5 M NaOH (15.5 mmol) was added, and stirring was continued for another 2 days. The THF was removed under reduced pressure, then the aqueous residue was acidified with 1 M HCl to pH 5 and extracted with diethyl ether. The combined organic layers were washed with brine and dried over $MgSO_4$. The diethyl ether was removed under reduced pressure, and the resulting crude powder was recrystalized in hexanes to yield 15.1 g (78%) of white powder 16a. Mp 114-116° C. $^1$H-NMR (400 MHz, $CDCl_3$, $\delta_H$ ppm): 7.43 (6H, m, p-Ar), 7.28 (6H, m, m-Ar), 7.22 (3H, m, o-Ar), 3.05 (2H, t, $^3J_{H-H}$=6.4 Hz, HO—$CH_2$), 2.33 (2H, t, $^3J_{H-H}$=7.5 Hz, $CH_2CO_2$), 1.56-1.68 (4H, m, $2CH_2$), 1.36-1.47 (2H, m, $CH_2$). $^{13}$C-NMR (100 MHz, $CDCl_3$, $\delta_H$ ppm): 180.26, 144.36, 128.62, 127.66, 126.79, 86.30, 63.24, 33.98, 29.63, 25.74, 24.48. HRMS (EI): m/z calcd 374.1882 ($C_{25}H_{26}O_3$), found 374.1883 [M]$^+$.

9-Trityloxy-nonanoic acid (16b).

Aqueous 0.5 M NaOH (13.2 mL, 6.6 mmol) was added to a stirring solution of 15b (1.41 g, 3.3 mol) in 25 mL of THF. The reaction mixture was stirred for 3 days at room temperature, and then the solvent was removed by rotary evaporation. The purification was carried out by flash column chromatography (gradient 10% EtOAc in hexanes to 100% EtOAc) to obtain 1.28 g (93%) of a pale yellow oil 16b. $^1$H-NMR (400 MHz, $CDCl_3$, $\delta_H$ ppm): 7.43 (6H, m, p-Ar), 7.28 (6H, m, m-Ar), 7.21 (3H, m, o-Ar), 3.03 (2H, t, $^3J_{H-H}$=6.6 Hz, HO—CH$_2$), 2.33 (2H, t, $^3J_{H-H}$=7.5 Hz, CH$_2$CO$_2$), 1.56-1.66 (4H, m, 2CH$_2$), 1.20-1.40 (8H, m, 4CH$_2$). $^{13}$C-NMR (100 MHz, CDCl$_3$, δ$_H$ ppm): 180.26, 144.46, 128.63, 127.64, 126.74, 86.22, 63.55, 34.04, 29.95, 29.24, 29.13, 28.96, 26.15, 24.60. HRMS (EI): m/z calcd 416.2351 (C$_{28}$H$_{32}$O$_3$), found 416.2360 [M]$^+$.

12-Trityloxy-dodecanoic acid (16c).

The synthesis and purification procedures of 16b were followed. Aqueous 0.5 M NaOH (4.6 mL, 2.3 mmol), 15c (548 mg, 1.2 mmol), and THF (9.3 mL) were used and the reaction duration was shortened to 2 days. After purification, 463 mg (87%) of 16c was obtained as a colorless oil. $^1$H-NMR (400 MHz, CDCl$_3$, δ$_H$ ppm): 7.43 (6H, m, p-Ar), 7.28 (6H, m, m-Ar), 7.21 (3H, m, o-Ar), 3.02 (2H, t, $^3J_{H-H}$=6.7 Hz, HO—CH$_2$), 2.34 (2H, t, $^3J_{H-H}$=7.5 Hz, CH$_2$CO$_2$), 1.55-1.67 (4H, m, 2CH$_2$), 1.19-1.39 (14H, m, 7CH$_2$). $^{13}$C-NMR (100 MHz, CDCl$_3$, δ$_H$ ppm): 180.02, 144.53, 128.69, 127.64, 126.75, 86.25, 63.66, 34.02, 30.04, 29.52, 29.50, 29.48, 29.39, 29.22, 29.05, 26.25, 24.66. HRMS (EI): m/z calcd 458.2821 (C$_{31}$H$_{38}$O$_3$), found 458.2814 [M]$^+$.

Ghrelin(1-5)-6C—F (17).

Selective Mtt amine deprotection was performed to residue-3 of 12 according to the general procedure and the side-chain precursor 16a was coupled following the general procedure for coupling. Deprotection of the trityl containing side-chain was conducted according to the general procedure to obtain free alcohol. This alcohol was then activated by an overnight treatment with tosyl chloride (47.66 mg, 0.25 mmol) in 2 mL of 50% CH$_2$Cl$_2$:50% pyridine mixture under argon to provide tosylated alcohol. Following this reaction, the resin was washed successively with CH$_2$Cl$_2$ and THF. Fluorination was then conducted by shaking the resin in 4 eq. of 0.1 M anhydrous TBAF in THF under argon for 2.5 hours, twice. Successive THF and CH$_2$Cl$_2$ washes were performed after each fluorination step. Following this, a final cleavage and deprotection was conducted according to the general procedure to obtain the crude peptide. Purification was performed by HPLC (gradient 20-40% solvent B in A) to obtain 17 as a white powder with an overall yield of 9% (3.4 mg). MS (ESI): m/z calcd 623.3, found 646.3 [M+Na]$^+$.

General Procedure for Fluorine Bearing Ghrelin(1-14) Analogues (18a, 18b, and 18c).

These peptides were made from on-resin peptide 13 following a procedure similar to the synthesis of 17. Side-chains 16a, 16b, and 16c were coupled to the peptide to obtain 18a, 18b, and 18c respectively after alcohol deprotection, activation, and fluorination steps. Mesylation was performed instead of tosylation as followed: resin was shaken with 5 eq. of MsCl and 15 eq. of NEt$_3$ in anhydrous CH$_2$Cl$_2$ under argon for 4 hours, and then after washing the process was repeated once more overnight. Fluorination was conducted in a similar manner using up to 9 eq. of 0.1 M anhydrous TBAF/THF and the process was repeated up to 6 times, as necessary for maximal fluorine incorporation.

Ghrelin(1-14)-6C—F (18a).

Purification was performed by HPLC (gradient 12-30% solvent B in A) to obtain 18a as a white powder with an overall yield of 7% (7.4 mg). MS (ESI): m/z calcd 1712.9, found 857.5 [M+2H]$^{2+}$, 572.0 [M+3H]$^{3+}$ (100%).

Ghrelin(1-14)-9C—F (18b).

Purification was performed by HPLC (gradient 25-50% solvent B in A) to obtain 18b as a white powder with an overall yield of 2% (2.2 mg). MS (ESI): m/z calcd 1754.9, found 1756.0 [M+H]$^+$, 889.5 [M+Na+H]$^{2+}$ (100%).

Ghrelin(1-14)-12C—F (18c).

Purification was performed by HPLC (gradient 25-40% solvent B in A) to obtain 18c as a white powder with an overall yield of 12% (12.1 mg). MS (ESI): m/z calcd 1797.0, found 899.5 [M+2H]$^{2+}$ (100%).

4-(Cyclopentadienylrhenium tricarbonyl)-4-oxobutanoic acid (19a).

This compound was prepared from CpRe(CO)$_3$ (1.00 g, 3.0 mmol) according to a literature procedure described in Salmain et al. *Bioconjugate Chemistry* 1993, 4, 425-433, the relevant contents of which are incorporated herein by reference. The yellow solid 19a was obtained with a yield of 37% (0.49 g). $^1$H-NMR (400 MHz, CDCl$_3$, δ$_H$ ppm): 6.00-6.04 (2H, m, Cp), 5.38-5.42 (2H, m, Cp), 2.87-2.93 (2H, m, CH$_2$), 2.72-2.78 (2H, m, CH$_2$). $^{13}$C-NMR (100 MHz, CDCl$_3$, δ$_H$ ppm): 192.97 (CO), 191.62 (CO), 177.12 (CO$_2$H), 95.15 (Cp-CO), 87.94 (Cp), 85.22 (Cp), 33.15 (CH$_2$), 27.44 (CH$_2$). HRMS (EI): m/z calcd 437.0029 ([M+H]$^+$, C$_{12}$H$_{10}$O$_6$$^{187}$Re), found 437.0022 [M+H]$^+$.

6-(Cyclopentadienylrhenium tricarbonyl)-6-oxohexanoic acid (19b).

Anhydrous AlCl$_3$ (2.67 g, 20.0 mmol) and succinic anhydride (1.28 g, 10.0 mmol) were dissolved in 100 mL of anhydrous CH$_2$Cl$_2$ under argon flow. CpRe(CO)$_3$ (1.68 g, 5.0 mmol) was added, and mixture was refluxed for 1 day. Ice cold 5 M HCl$_{aq}$ was added to the reaction mixture and the organic layer was removed. The aqueous layer was extracted by CH$_2$Cl$_2$ three times, the combined organic layers were dried over MgSO$_4$ and the solvent was removed under reduced pressure. After adding EtOAc, the insoluble byproducts were removed by filtration and purification was performed by column chromatography (20% EtOAc in hexanes, 50%, EtOAc in hexanes, then 1% HOAc in EtOAc) to obtain 1.30 g (56%) of yellow solid 19b. $^1$H-NMR (400 MHz, CDCl$_3$, δ$_H$ ppm): 5-96-6.00 (2H, m, Cp), 5.34-5.41 (2H, m, Cp), 2.59-2.66 (2H, t, $^3J_{H-H}$=7.0 Hz, CH$_2$CO), 2.36-2.43 (2H, t, $^3J_{H-H}$=6.9 Hz, CH$_2$CO), 1.63-1.79 (4H, m, 2CH$_2$). $^{13}$C-NMR (100 MHz, CDCl$_3$, δ$_H$ ppm): 194.66 (CO), 191.72 (CO), 178.90 (CO$_2$H), 95.86 (Cp-CO), 87.85 (Cp), 85.22 (Cp), 38.28 (CH$_2$CO), 33.58 (CH$_2$CO), 23.99 (CH$_2$), 23.52 (CH$_2$). HRMS (EI): m/z calcd 485.0139 ([M+Na]$^+$, C$_{14}$H$_{13}$O$_6$$^{185}$ReNa); found 485.0144 [M+Na]$^+$.

General Procedure for Rhenium Bearing Ghrelin(1-14) Analogues (20a and 20b).

Selective amine-Mtt deprotection was conducted to residue-3 of 13 according to the general procedure, and then the side-chain precursor 19a and 19b was coupled using the general coupling procedure. The peptides were cleaved off the resin and deprotected according to the general procedure to obtain crude peptides 20a and 20b.

Ghrelin(1-14)-4C-CpRe(CO)$_3$ (20a).

Purification was performed by HPLC (gradient 25-50% of solvent B in A) to obtain white powder 20a with an overall yield of 24% (55.6 mg). MS (ESI): m/z calcd 2014.8, found 1008.4 [M+2H]$^{2+}$.

Ghrelin(1-14)-6C-CpRe(CO)$_3$ (20b).

Purification was performed by HPLC (gradient 20-40% of solvent B in A) to obtain white powder 20b with an overall yield of 36% (43.3 mg). MS (MALDI-TOF): m/z calcd 2042.8, found 2043.8 [M+H]$^+$.

Radioligand Binding Assay.

Determination of IC$_{50}$ values of ghrelin analogues 17, 18a-c, and 20a-b for GHSR were conducted by radioligand binding assays according to published literature procedures (Katugampola et al. *British Journal of Pharmacology* 2001, 134, 143-149, the relevant contents of which are incorporated herein by reference). Assays were performed using human recombinant CHO—K1 cells as receptor source and $^{125}$I- ghrelin (human) as radioligand. Reference standard using ghrelin (human) were run to ensure the validity of the results. $IC_{50}$ values were determined by a non-linear, least squares regression analysis using MathIQ™ (ID Business Solutions Ltd., UK). Ghrelin(1-5)-6C—F 17 exhibited about 20% inhibition at 2000 nM (reported as an $IC_{50}$ of >2000 nM). For ghrelin(1-14) analogues 18a-c and 20a-b, $IC_{50}$ values were determined semi-quantitatively according to % inhibition at $10^{-5}$, $10^{-6}$, $10^{-7}$, and $10^{-8}$ M concentration (all data duplicated). $IC_{50}$ values are reported in Tables 1 and 2.

TABLE 1

Binding Affinity Data of Fluorine Bearing Ghrelin Analogues

| Cmpd | Purity (%) | m/z | | $IC_{50}$ (nM) |
| --- | --- | --- | --- | --- |
| | | calcd | obsd | |
| 17 | 97 | $[M + Na]^+$ 646.3 | 646.3 | >2000 |
| 18a | 98 | $[M + 2H]^{2+}$ 857.4 | 857.5 | 147 |
| 18b | 99 | $[M + H]^+$ 1755.9 | 1756.0 | 39.6 |
| 18c | 99 | $[M + 2H]^{2+}$ 899.5 | 899.5 | 27.9 |

TABLE 2

Binding Affinity Data of Rhenium Bearing Ghrelin Analogues

| Cmpd | Purity (%) | m/z | | $IC_{50}$ (nM) |
| --- | --- | --- | --- | --- |
| | | calcd | obsd | |
| 20a | 98 | $[M + 2H]^{2+}$ 1008.4 | 1008.4 | 35 |
| 20b | 99 | $[M + H]^+$ 2043.8 | 2043.8 | 174 |

Results and Discussion
Fluorine Bearing Ghrelin Analogues

Figure 2:
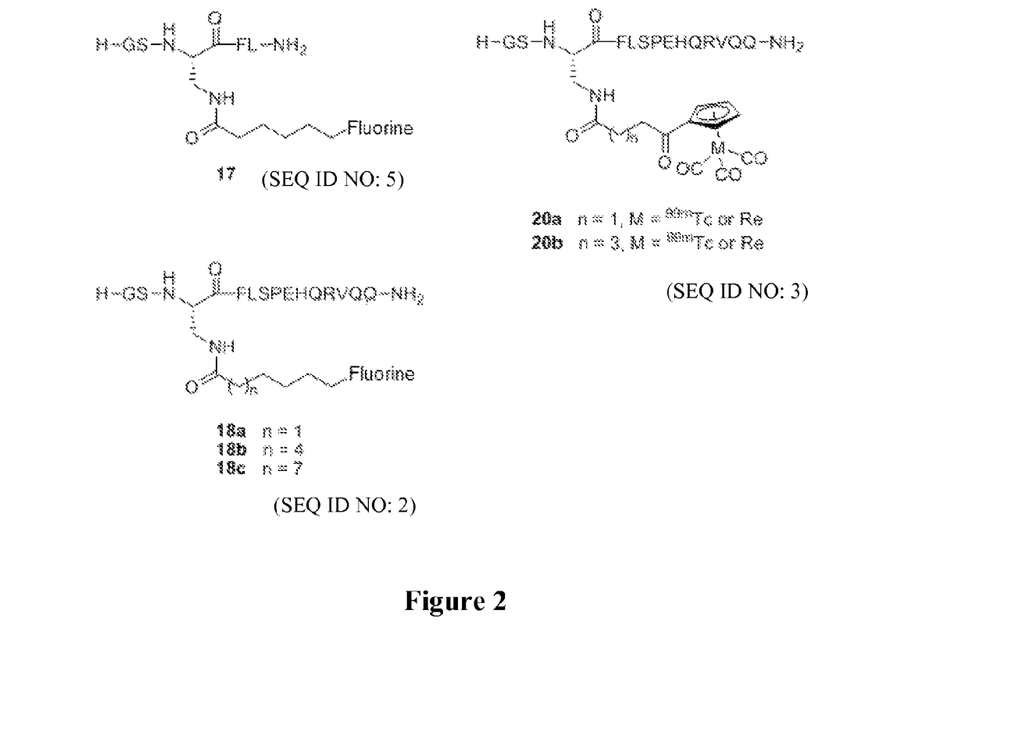
FIG. 2 illustrates the chemical structures of ghrelin analogues according to embodiments of the present invention.

The peptides were assembled following standard 9-fluorenylmethoxycarbonyl (Fmoc) solid phase peptide synthesis (SPPS) methods on a polystyrene-based insoluble support, Rink amide 4-methylbenzhydrylamine (MBHA) resin, which provided an amide C-terminus upon cleavage. The Ser-3 of human ghrelin was replaced with Dpr, protected by the weak acid labile methyltrityl (Mtt), to provide an amide linkage in this position upon further modification. The fully-protected resin-bound ghrelin(1-5) 12 and ghrelin(1-14) 13 prior to modification are shown in FIG. 2.

At this point, the Dpr-3 of the peptide was ready for functionalization. Fluorine bearing analogues were designed with the fluorine attached to the end of the aliphatic side-chain with variable length. Non-radioactive analogues using $^{19}F$ in the place of $^{18}F$ were used to study their chemical and biological properties and side-chain precursors were prepared in solution phase prior to attachment to the peptide, with fluorination of the side-chain being conducted on-resin. Prior to attachment, side-chain precursors had three features: an aliphatic chain with length adjusted for binding affinity to the receptor, a site of attachment to the peptide, and a site of attachment for the imaging agent.

Figure 3:
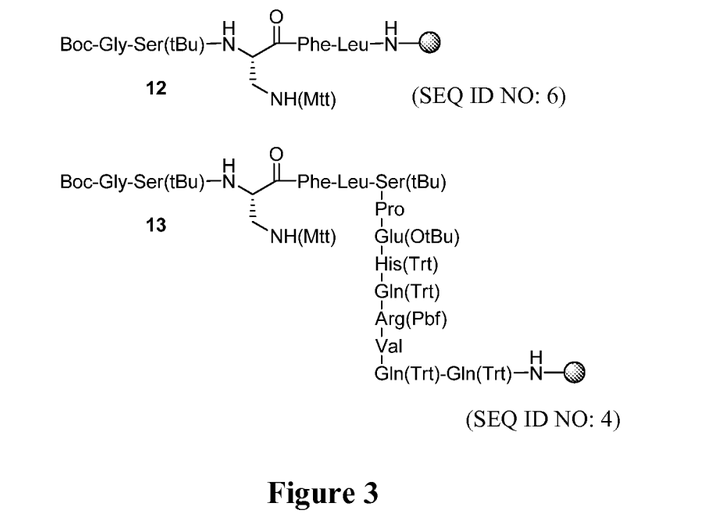
FIG. 3 illustrates the chemical structures of intermediates in the preparation of truncated ghrelin analogues.
Figure 4:
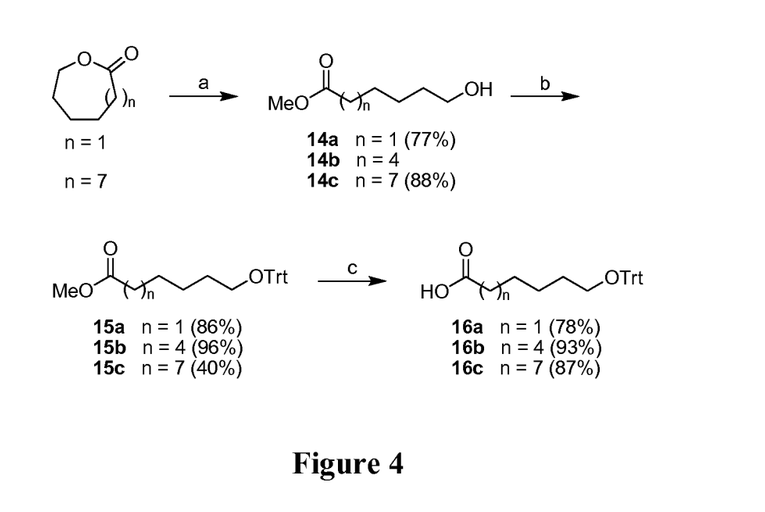
FIG. 4 illustrates the synthesis of side-chain precursors for incorporation into ghrelin analogues.
Figure 5:
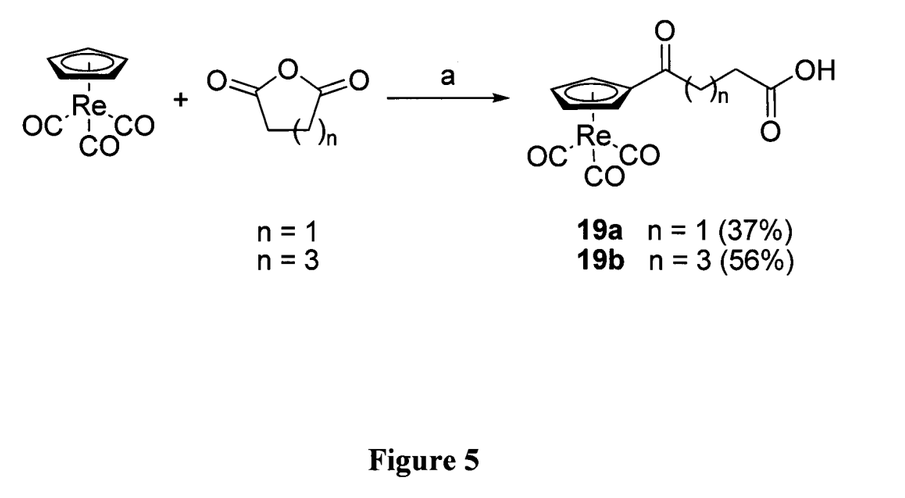
FIG. 5 illustrates the synthesis of organometallic side-chain precursors for incorporation into ghrelin analogues.

Three different side-chain lengths were prepared: 6, 9, and 12 carbon length, indicated as 6C, 9C, and 12C respectively. The 6C and 12C precursors were prepared from their cyclic lactones, with the first synthetic step being the opening of the lactone rings in methanol using an acid catalyst (FIG. 3). Methanol was chosen as media to provide methyl protection to the carboxylate group. The formed alcohols 14a and 14c, as well as commercially available methyl-9-hydroxynonanoate, the starting material for 9C, were then tritylated to obtain weak acid labile protection for the alcohol group, which was necessary during the side-chain coupling to the peptide. Purification of the tritylated products 15a, 15b, and 15c was problematic and attempts to perform chromatography were made. The existence of excess trityl chloride and pyridinium salt made it difficult to dissolve the crude material and methanol was added to help the solvation. Unfortunately methanol reacted with unused trityl chloride, caused acid formation, and resulted in trityl (Trt) deprotection from the product that reformed the starting materials. Instead, the byproducts were removed by filtration with organic solvents at 0° C. to obtain 15a and 15b, or by flash chromatography without methanol to obtain 15c.

Hydrolysis of the methyl ester of 15a, 15b, and 15c was carried out under basic conditions, followed by an acidic work up, during which the pH was maintained above 4 to prevent trityl deprotection. After recrystallization for solid product or flash chromatography for oil products, 6-trityloxyhexanoic acid 16a, 9-trityloxynonanoic acid 16b and 12-trityloxydodecanoic acid 16c were isolated, providing aliphatic side-chains that were ready to be coupled to 12 and 13.

The on-resin reaction series started with a selective deprotection of the acid labile amine-Mtt of Dpr-3, which was done with a series of treatments with a dilute trifluoroacetic acid (2% TFA) solution in $CH_2Cl_2$. After the free amine was obtained, the carboxylic acid group of the side-chain precursor was coupled to this amine via O-benzotriazole (OBt) ester formation, following standard coupling procedures in peptide synthesis. For the 5-mer 12, only 16a was coupled to the peptide, while for the 14-mer 13, all precursors previously made, 16a, 16b, and 16c, were used. Reaction completion was followed by the Kaiser Test and in some cases micro cleavage to allow HPLC analysis and MS analysis to confirm the product mass.

After the side-chain was attached to the peptide, the protected alcohol was transformed to a fluoro group via several steps. The first step was the selective deprotection of the alcohol-Trt with dilute acid (2% TFA) solution in $CH_2Cl_2$. The obtained alcohol was activated prior to fluorination. For the ghrelin(1-5)-6C—OH, activation was done via tosylation in basic conditions. HPLC monitoring and MS analysis of the micro-cleaved product showed conversion of the starting material to the desired product ghrelin(1-5)-OTs (55%) and various byproducts. Mesylation was used for the 14-mer peptides for the reason that mesyl chloride (MsCl) forms a highly reactive intermediate sulfene ($SO_2CH_2$), in which the sulfur is highly electrophilic and will react with any alcohol, even with tertiary alcohols that react very slowly with TsCl. HPLC and MS analyses of the micro-cleaved products showed that mesylation was successfully applied to the 14-mer peptides with the 6C, 9C, and 12C side-chains.

Fluorination for both ghrelin(1-5) and ghrelin(1-14) derivatives was performed using tetra-n-butylamonium fluoride (TBAF) in tetrahydrofuran (THF), monitored by HPLC and MS analysis of micro-cleaved products. Fluorination was the last step done on-resin, and at this point the peptides were ready to be cleaved off the resin and fully deprotected. The desired fluorine bearing ghrelin(1-5)-6C—F 17, ghrelin(1-14)-6C—F 18a, ghrelin(1-14)-9C—F 18b, and ghrelin(1-14)-12C—F 18c were isolated with yields of 9%, 7%, 2%, and 12% respectively (Table 2).

The binding affinities of these fluorine bearing ghrelin(1-5) and ghrelin(1-14) derivatives to the GHSR were evaluated according to the half maximal inhibitory concentration ($IC_{50}$) values (Table 2) as determined by a radioligand binding assay. Fluorine bearing ghrelin(1-14) derivatives of different side-chain lengths: 6C, 9C, and 12C, were found to have satisfactory nanomolar binding affinities that make them suitable for use as imaging agents.

Rhenium Bearing Ghrelin Analogues

The second class of molecules designed were rhenium bearing ghrelin analogues to investigate the suitability of $^{99m}$Tc-radiolabelled ghrelin analogues as SPECT imaging agents for the GHSR. Cyclopentadienyl tricarbonyl organometallic (CpM(CO)$_3$) species were incorporated into the ghrelin analogues to impart imaging utility due to the neutral, lipophilic, and stable properties of this complex. The ability to use the cyclopentadienyl-metal complex in an integrated fashion, e.g. directly associated with the estrogen receptor binding site, was desirable. The neutral and lipophilic properties of the metal complex assisted in this integration of the complex as part of the residue-3 side-chain that participates in the binding to the GHSR.

The side-chains for the rhenium bearing ghrelin were prepared using solution-phase chemistry prior to attachment to the peptide. Two different lengths were prepared: 4 and 6 carbons long, counted from the amide's carbon to the carbon in which Cp ring is attached, and will be identified as 4C and 6C. Both precursors were prepared from their cyclic anhydride, succinic anhydride and adipic anhydride for 4C and 6C respectively, and rhenium tricarbonyl cyclopentadienyl (CpRe(CO)$_3$) through Friedel Crafts acylation using aluminum chloride (AlCl$_3$) (Scheme 4). The reaction for the 4C precursor went slowly and did not go to completion, due to the low reactivity of the Cp ring when it is coordinated to Re(I). The starting material CpRe(CO)$_3$ was recovered during the extraction, and the product 4-(Cyclopentadienylrhenium tricarbonyl)-4-oxobutanoic acid 19a, was isolated upon chromatography.

In the synthesis of 6C precursor, adipic anhydride was prepared from adipic acid through dehydration. In this regard, 2 eq. of adipic anhydride and 4 eq. of AlCl$_3$ were used, CH$_2$Cl$_2$ was used as the solvent, and the mixture was refluxed. This caused all starting material to be consumed within 2 days and upon purification, 6-(Cyclopentadienylrhenium tricarbonyl)-6-oxohexanoic acid 19b, as well as the dimer 1,6-di(CpRe(CO)$_3$)-1,6-dioxohexane as a byproduct, were isolated.

The side-chain precursors 19a and 19b, already containing rhenium, were ready to be incorporated into the peptide at this point. Fully protected on-resin 13 was prepared and the Mtt group was removed from the amine of Dpr-3 using 2% TFA solution. The side-chains 19a and 19b were then coupled to this amine followed by cleaving from resin and complete deprotection. The rhenium bearing ghrelin(1-14)-4C-CpRe(CO)$_3$ 20a and ghrelin(1-14)-6C-CpRe(CO)$_3$ 20b were obtained with purified yields of 24% and 36% respectively (Table 2).

The evaluation of 20a and 20b showed that both molecules have good binding affinity to the GHSR, marked by their nanomolar IC$_{50}$ values: 35 nM and 174 nM respectively (Table 2). The incorporation of a metal complex in the binding region of a peptide ligand was a success, with the neutral and lipophilic complex, CpRe(CO)$_3$, which mimicked the lipophilic property of the original ghrelin side-chain.

This work demonstrates that analogues of ghrelin have strong affinity to a receptor target, and thus, are suitable for use as probes for the non-invasive imaging of tumours expressing a receptor target, as well as for use as a carrier to deliver a therapeutic agent to a target receptor in, for example, a tumour.

Example 2

Fluorescein-Labelled Ghrelin Analogues for Breast Cancer Cell Studies

Materials:

Unless otherwise stated, all reagents and solvents were ACS grade or higher and used without further purification from commercial suppliers. Fmoc-protected amino acids, HBTU, and rink amide p-methylbenzylhydrylamine (MBHA) resin (0.52 meq/g) were obtained from Peptide International (Louisville, Ky.). Fmoc-Dap (Alloc)-OH was obtained from Chem-Impex (Wood Dale, Ill.). Octanoic acid and fluorescein isothiocynate (FITC) isomer I was obtained from Aldrich (Oakville, ON). Cell culture medium minimum essential medium alpha (αMEM), Fetal Bovine Serum (FBS), Penicillin-Streptomycin (PEST) and Trypsin were purchased from GIBCO and Invitrogen (Carlsbad, Calif.).

Figure 6:
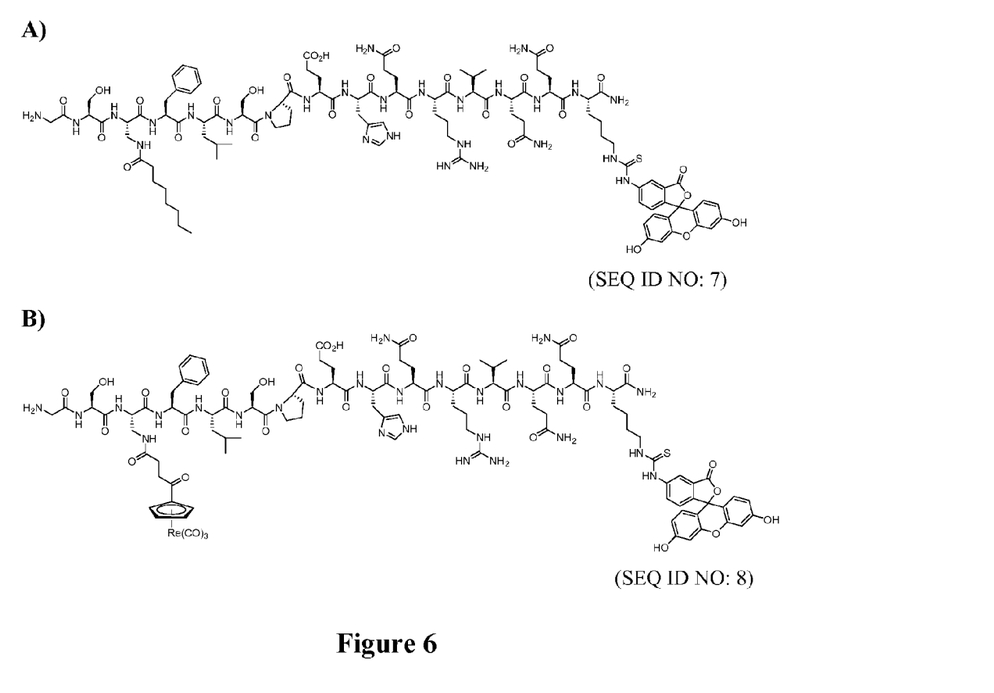
FIG. 6 illustrates the chemical structures of ghrelin analogues (A and B) used in cell binding studies.

Peptide Synthesis:

Elongation of peptidyl chains on rink amide MBHA resins (1 mmol) was performed on an automated synthesizer (APEX396 peptide synthesizer) using manufacturer supplied protocols. The peptidyl resin was then transferred to a manual peptide vessel and the Alloc group from the side chain of diamonipropionic (Dap) acid (residue-3) was removed using tetrakis(triphenylphosphine)palladium(0) and phenylsilane (2×30 min at room temperature) under argon atmosphere. The resin was washed successively with DCM, THF, and DMF after each coupling. The resin was then agitated (at 600 rpm) for 4 hours with HBTU (3 equiv), catalytic amount of diisopropylamine (DIPEA) (6 equiv) and either 4-fold excess of octanoic acid or 4-(cyclopentadienylrhenium tricarbonyl)-4-oxobutanoic acid in dimethylformide (DMF). The trityl group from the side chain of Lys (residue-15) was removed with 1% trifluoroacetic acid (TFA) in dichloromethane (7×2 min). Again, successive washes with DMF, DCM and THF were performed after each deprotection step. Subsequently, the peptidyl resin was vigorously stirred for 4 hours with FITC (3 equiv) and DIPEA (6 equiv) in DMF. The ensuing resin was treated with cleavage cocktail consisting of 88% TFA and 12% scavengers (5% water, 5% triisopropylsilane, and 2% phenol). The resulting suspension was shaken for 4 hours at 700 rpm. The filtrate was collected, filtered into cold tert-butyl methyl ether and pelleted via centrifugation at 3000 rpm and –5° C. for 10 minutes. Pellets were then dissolved in distilled-deionized water and lyophilized yielding yellow solids for both analogs. Crude peptides were analyzed by analytical reverse-phase high-pressure liquid chromatography (HPLC) on a Grace Vydac protein/peptide RP-C18 column 4.6×250 mm, 5 µm. Preparative separations of peptides was done on a Grace Vydac protein/peptide RP-C18 column 22×250 mm, 10 µm, followed by analytical hplc for purity analysis. Characterization was performed using electro-spray mass spectrometry (MS) in the positive-ion mode on a Waters Quattro Micro MS/MS. The structures of the peptides synthesized are shown in FIG. 6A [Dpr$^3$(COC$_7$H$_{15}$), Lys$^{15}$(FITC)]-ghrelin(1-14) amide and FIG. 6B [Dpr$^3$(COC$_2$H$_4$COCpTR), Lys$^{15}$(FITC)]-ghrelin(1-14) amide.

Cell Uptake Studies:

MDA-231-LN cells were grown in αMEM medium supplemented with FBS and PEST. Cells seeded in a 6-well dish in 500 µL medium (confluency of 200,000 cells/well) were used for experiments performed in duplicates one day after seeding. Cells used for uptake experiments were washed two times with ice-cold PBS buffer and incubated (at 37° C. for 60 minutes) with 10 µL of 5 mM or 0.5 mM FITC-conjugated ghrelin peptides in DMSO to give a final concentration of 100 μM and 10 μM, respectively. Cells used for blocking studies were treated with 10 μL of 5 mM FITC-conjugated ghrelin peptides and 10 μL of 50 mM hexarelin in DMSO. Negative control received no peptide or block treatments. Following incubation, cells were washed 5 times with PBS containing 5% FBS to remove any remaining extracellular peptides.

Flow Cytometry:

MDA-231-LN breast cancer cells were dissociated with trypsin (0.25%), and washed five times with PBS containing 5% FBS. Then, the cells were re-suspended in PBS containing 5% FBS. Cells were immediately analyzed on COPAS (Complex Object Parametric Analyzer and Sorter) Select System equipped with an argon laser (488 nm excitation wavelength) for quantitative fluorescence analysis, utilizing the Profiler II acquisition and analysis software. Excitation Fluorescence was measured using a 525 nm band-pass filter. Approximately 10,000 cells per treatment were analyzed. Data was exported to Microsoft Excel for further analysis.

Figure 7:
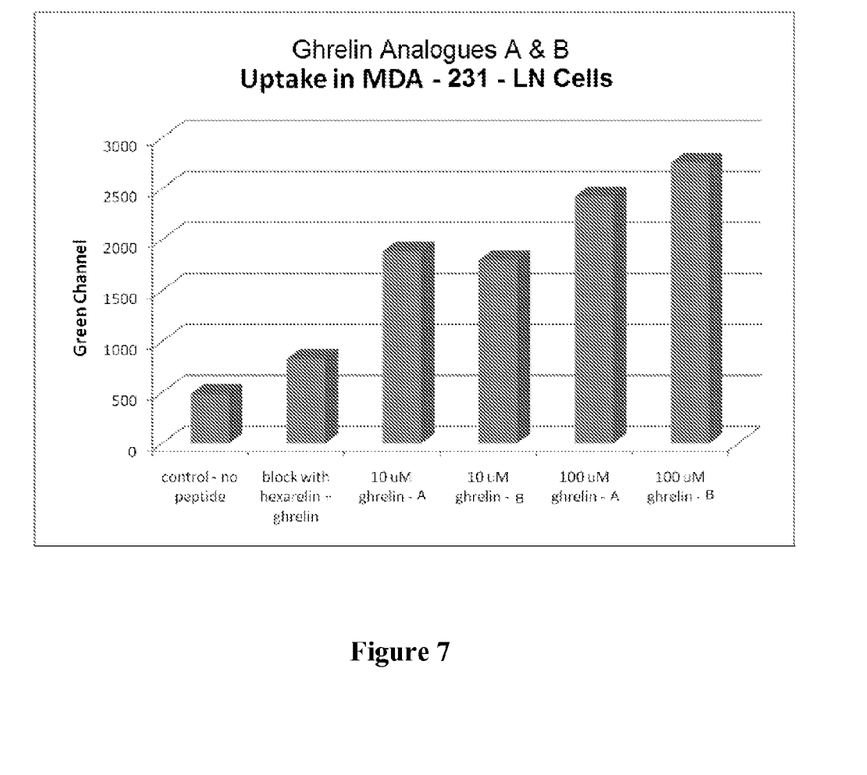
FIG. 7 graphically illustrates the results of ghrelin analogue cell binding studies.

Results:

As shown in FIG. 7, the labelled ghrelin analogues successfully exhibited concentration-dependent cell-binding to the cancer cells confirming their utility for imaging.

We claim:

1. A ghrelin analogue comprising a peptide comprising a sequence ranging from at least amino acid residues 1-7 of SEQ ID NO: 1 to a sequence of up to amino acid residues 1-28 of SEQ ID NO: 1 and an imaging agent, wherein said imaging agent is attached to the peptide at the amino acid residue at position 3 of SEQ ID NO: 1 via a linker which consists of an amide linkage and 4 to 12 methylene or an aromatic entity selected from the group consisting of phenyl, biphenyl, naphthyl and cyclopentyldienyl, and wherein the imaging agent and linker replace the n-octanoyl group of SEQ ID NO: 1 and the ghrelin analogue retains receptor-binding activity.

2. A composition comprising a ghrelin analogue as defined in claim 1 and a pharmaceutically acceptable adjuvant.

3. The analogue of claim 1, wherein the peptide comprises at least amino acid residues 1-10 of SEQ ID NO: 1.

4. The analogue of claim 1, wherein the imaging agent is selected from the group consisting of single photon emission computed tomography, positron emission tomography, magnetic resonance imaging, computed tomography, optical imaging and ultrasound.

5. The analogue of claim 1, wherein the imaging agent is selected from the group consisting of $^{67}$Ga, $^{99m}$Tc, $^{111}$In, $^{123}$I, $^{18}$F, $^{44}$Sc, $^{64}$Cu, $^{68}$Ga, $^{94m}$Tc, a lanthanide, an iron oxide and a fluorescent dye.

6. The analogue of claim 1, wherein the imaging agent is a positron emitting radionuclide.

7. The analogue of claim 6, wherein the imaging agent is selected from the group consisting of $^{18}$F, $^{44}$Sc, $^{64}$Cu, $^{68}$Ga, and $^{94m}$Tc.

* * * * *

```
                           SEQUENCE LISTING

<160> NUMBER OF SEQ ID NOS: 8

<210> SEQ ID NO 1
<211> LENGTH: 28
<212> TYPE: PRT
<213> ORGANISM: Artificial Sequence
<220> FEATURE:
<223> OTHER INFORMATION: ghrellin analogue
<220> FEATURE:
<221> NAME/KEY: MISC_FEATURE
<222> LOCATION: (3)..(3)
<223> OTHER INFORMATION: Serine at position 3 includes an n-octanyl
      group

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 14
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (3)..(3)
<223> OTHER INFORMATION: Serine at position 3 is substituted with CNC(O)
      (CH2)nFluorine, wherein n=5, 8 or 11

<400> SEQUENCE: 2

Gly Ser Ser Phe Leu Ser Pro Glu His Gln Arg Val Gln Gln
1               5                   10

<210> SEQ ID NO 3
<211> LENGTH: 14
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (3)..(3)
<223> OTHER INFORMATION: Serine at position 3 is substituted with
      CNC(O)(CH2)n-cyclopentadienyl-M-tricarbonyl, wherein n=2 or 4 and
      M is a metal

<400> SEQUENCE: 3

Gly Ser Ser Phe Leu Ser Pro Glu His Gln Arg Val Gln Gln
1               5                   10

<210> SEQ ID NO 4
```

```
<211> LENGTH: 14
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (1)..(1)
<223> OTHER INFORMATION: Glycine is protected by Boc
<220> FEATURE:
<221> NAME/KEY: MISC_FEATURE
<222> LOCATION: (2)..(2)
<223> OTHER INFORMATION: Serine is protected by tBu
<220> FEATURE:
<221> NAME/KEY: MISC_FEATURE
<222> LOCATION: (3)..(3)
<223> OTHER INFORMATION: Serine is replaced by diaminopropanoic acid
      protected by methytrityl
<220> FEATURE:
<221> NAME/KEY: MISC_FEATURE
<222> LOCATION: (6)..(6)
<223> OTHER INFORMATION: Serine is protected by tBu
<220> FEATURE:
<221> NAME/KEY: MISC_FEATURE
<222> LOCATION: (8)..(8)
<223> OTHER INFORMATION: Glu is protected by OtBu
<220> FEATURE:
<221> NAME/KEY: MISC_FEATURE
<222> LOCATION: (9)..(10)
<223> OTHER INFORMATION: Protected by Trt
<220> FEATURE:
<221> NAME/KEY: MISC_FEATURE
<222> LOCATION: (11)..(11)
<223> OTHER INFORMATION: Protected by Pbf
<220> FEATURE:
<221> NAME/KEY: MISC_FEATURE
<222> LOCATION: (13)..(14)
<223> OTHER INFORMATION: Protected by Trt
<220> FEATURE:
<221> NAME/KEY: MISC_FEATURE
<222> LOCATION: (14)..(14)
<223> OTHER INFORMATION: Gln linked to a resin

<400> SEQUENCE: 4

Gly Ser Ser Phe Leu Ser Pro Glu His Gln Arg Val Gln Gln
1               5                   10

<210> SEQ ID NO 5
<211> LENGTH: 5
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (3)..(3)
<223> OTHER INFORMATION: Serine at position 3 is substituted with CNC(O)
      (CH2)5-Fluorine

<400> SEQUENCE: 5

Gly Ser Ser Phe Leu
1               5

<210> SEQ ID NO 6
<211> LENGTH: 5
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (1)..(1)
<223> OTHER INFORMATION: Glycine is protected by Boc
<220> FEATURE:
<221> NAME/KEY: MISC_FEATURE
<222> LOCATION: (2)..(2)
```

```
<223> OTHER INFORMATION: Serine is protected by tBu
<220> FEATURE:
<221> NAME/KEY: MISC_FEATURE
<222> LOCATION: (3)..(3)
<223> OTHER INFORMATION: Serine is replaced by diaminopropanoic acid
      protected by methytrityl
<220> FEATURE:
<221> NAME/KEY: MISC_FEATURE
<222> LOCATION: (5)..(5)
<223> OTHER INFORMATION: Leucine is bound to a resin

<400> SEQUENCE: 6

Gly Ser Ser Phe Leu
1               5

<210> SEQ ID NO 7
<211> LENGTH: 16
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (3)..(3)
<223> OTHER INFORMATION: Serine at position 3 is substituted with CNC(O)
      (CH2)7
<220> FEATURE:
<221> NAME/KEY: MISC_FEATURE
<222> LOCATION: (15)..(15)
<223> OTHER INFORMATION: Lysine is bound to fluorescein isothiocyanate

<400> SEQUENCE: 7

Gly Ser Ser Phe Leu Ser Pro Glu His Gln Arg Val Gln Gln Arg Lys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: ghrelin analogue
<220> FEATURE:
<221> NAME/KEY: MISC_FEATURE
<222> LOCATION: (3)..(3)
<223> OTHER INFORMATION: Serine at position 3 is substituted with
      CNC(O)(CH2)2-cyclopentadienyl-rhenium-tricarbonyl
<220> FEATURE:
<221> NAME/KEY: MISC_FEATURE
<222> LOCATION: (15)..(15)
<223> OTHER INFORMATION: Lysine is bound to fluorescein isothiocyanate

<400> SEQUENCE: 8

Gly Ser Ser Phe Leu Ser Pro Glu His Gln Arg Val Gln Gln Arg Lys
1               5                   10                  15
```